United States Patent
Lloyd et al.

(10) Patent No.: US 6,579,276 B2
(45) Date of Patent: Jun. 17, 2003

(54) OCULAR IONTOPHORETIC DEVICE AND METHOD FOR INHIBITING VASCULAR ENDOTHELIAL GROWTH FACTOR (VEGF) USING THE SAME

(75) Inventors: Lindsay B. Lloyd, Salt Lake City, UT (US); Thomas M. Parkinson, White Salmon, WA (US); Malgorzata Szlek, Salt Lake City, UT (US)

(73) Assignee: Iomed, Inc., Salt Lake City, UT (US)

( * ) Notice: Subject to any disclaimer, the term of this patent is extended or adjusted under 35 U.S.C. 154(b) by 0 days.

(21) Appl. No.: 09/767,032

(22) Filed: Jan. 22, 2001

(65) Prior Publication Data

US 2002/0099358 A1 Jul. 25, 2002

(51) Int. Cl.$^7$ ................................. A61N 1/30
(52) U.S. Cl. .................. 604/521; 604/501; 604/20; 424/427
(58) Field of Search .................. 604/20, 890.1, 604/500–501, 521, 289–290, 294; 424/422, 424–425, 427

(56) References Cited

U.S. PATENT DOCUMENTS 5,676,648 A * 10/1997 Henley ................... 604/20
6,319,240 B1 * 11/2001 Beck ....................... 604/20

\* cited by examiner

*Primary Examiner*—Brian L. Casler
*Assistant Examiner*—LoAn H. Thanh
(74) *Attorney, Agent, or Firm*—Factor & Partners

(57) ABSTRACT

An ocular iontophoretic device for delivering an aptamer to an affected area of a living being's eye for inhibiting VEGF function therein, the device comprising an active electrode assembly associated with a matrix and/or reservoir, wherein the matrix and/or reservoir includes an aptamer capable of inhibiting VEGF function.

A method for treating an affected area of a living being's eye, comprising the steps of: associating an aptamer with an ocular iontophoretic device; positioning at least a portion of an ocular iontophoretic device on the eye of the living being; and iontophoretically delivering the aptamer to an affected area of the living being's eye.

22 Claims, 1 Drawing Sheet

OCULAR IONTOPHORETIC DEVICE AND METHOD FOR INHIBITING VASCULAR ENDOTHELIAL GROWTH FACTOR (VEGF) USING THE SAME

BACKGROUND OF THE INVENTION

1. Field of the Invention

The present invention relates in general to an ocular iontophoretic device, and more particularly, to an ocular iontophoretic device which, upon association with the eye of a living being, and application of an electrical potential difference, iontophoretically delivers an aptamer into the living being's eye, thereby inhibiting VEGF function therewithin.

2. Background Art

Vascular Endothelial Growth Factor (VEGF) is a protein that stimulates the growth of new blood vessels in the body of a living being, which has been identified in the art as angiogenesis and/or neovasculation. VEGF is presently believed to comprise four isoforms, including VEGF-121, VEGF-165, VEGF-189, and VEGF-206, which are believed to be the result of alternative splicing of mRNA. Of these isoforms, VEGF-165 is the most abundant, amounting to approximately 90% of the total VEGF.

VEGF was originally identified as a factor which increased the permeability of vascular tissues; consequently it is also known as Vascular Permeability Factor (VPF). VEGF is, therefore, a factor in causation of edema as well as neovascularization.

While normal blood vessel growth within a living being's eye is desirous for healthy tissues and surrounding structures, abnormal blood vessel growth and edema facilitated, at least in part by VEGF, can contribute to numerous eye diseases, including vision impairment, blindness, and the growth of malignant tumors—just to name a few. For example, Age-Related Macular Degeneration (AMD) is a leading cause of blindness in people aged 65 and older. The disease is characterized by the abnormal growth of new blood vessels into the macula of the retina. These new vessels are generally leaky and edematous. When the blood vessel leaks, scars form on the retina, leading to vision impairment, and sometimes, complete loss of vision.

One solution to the problems associated with VEGF and the undesirable, abnormal formation of new blood vessels, is to bind or attach an aptamer to VEGF—thus inactivating it by rendering it incapable of binding to its receptor in the vascular tissue. Recent studies have indicated that when an aptamer binds to VEGF, the VEGF function is slowed or stopped, thereby slowing or stopping the undesirable, abnormal growth of blood vessels.

While binding an aptamer to VEGF has been identified as a mechanism to inhibit the formation of new blood vessels, heretofore, problems associated with delivery of an aptamer to an affected area of a living being's eye has remained problematic. Indeed, known prior art devices and associated methods of delivering an aptamer, identified hereinbelow, are replete with drawbacks and disadvantages.

For example, delivering an aptamer to an affected, local area of a living being's eye using a systemic delivery method is problematic because of the many conventional side effects associated with systemic delivery, including unnecessary medicament exposure to unaffected areas, toxicity buildup, concentration control—just to name a few.

Local delivery of an aptamer via interocular injection is problematic, because of the opportunity for, among other things, retinal detachment, bleeding into the interior of the eye, increased interocular pressure, and increased risk of secondary infection. Although perhaps justifiable for occasional acute conditions, these risk factors render interocular injection undesirable as a delivery mode for chronic administration. Furthermore, interocular injections can be scary, unpleasant, and painful for the patient.

In addition to the above-identified problems associated with interocular injection, peribular or subconjuctival injection of an aptamer is problematic, because such injections may not deliver sufficient quantities to the interior of the eye. Moreover, peribular or subconjuctival injections are demanding of the physician inasmuch as placement of the needle requires an extremely high level of precision.

Topical administration of an aptamer to an affected, local area of a living being's eye is problematic due to its ineffectiveness for many applications, including affected areas in the back of the eye.

SUMMARY OF THE INVENTION

The present invention is directed to an ocular iontophoretic device for delivering an aptamer to an affected area of a living being's eye for inhibiting VEGF function therein, comprising an active electrode assembly associated with a matrix, wherein the matrix includes an aptamer capable of inhibiting VEGF function.

In a preferred embodiment of the invention, the matrix includes an aptamer capable of inhibiting at least one VEGF selected from the group consisting of VEGF-121, VEGF-165, VEGF-189, and VEGF-206, such as NX-1838.

In another preferred embodiment of the invention, the matrix also includes a PEGylating agent, reversibly attached to an aptamer, which slows enzymatic tissue digestion of the aptamer upon delivery of the same to the affected area of the living being's eye.

In yet another preferred embodiment of the invention, the aptamer is present in a concentration between approximately 0.1 milligrams (mg) and approximately 10 mg of aptamer per milliliter (ml) of water, and the water is buffered to a pH ranging between approximately 6.5 and approximately 8.5.

Preferably, the affected area of the eye is selected from at least one of the group consisting of the vitreous humor, retina, choroid, circulation of the retina, circulation of the choroid, and sclera.

It is also contemplated that the above-identified ocular iontophoretic device further comprises: (a) a counter electrode assembly, wherein the counter electrode assembly is configured for completing an electrical circuit between the active electrode assembly and an energy source; and (b) an energy source for generating an electrical potential difference.

The present invention is also directed to an ocular iontophoretic device for delivering an aptamer to an affected area of a living being's eye for inhibiting VEGF function therein, comprising: (a) a reservoir, wherein the reservoir includes an aptamer capable of inhibiting VEGF function; (b) a matrix, wherein the matrix is capable of temporarily retaining a solution having an aptamer; (c) an active electrode assembly associated with the matrix, wherein the active electrode assembly is configured for iontophoretically delivering the aptamer to the affected area of the living being's eye; (d) a counter electrode assembly, wherein the counter electrode assembly is configured for completing an electrical circuit between the active electrode assembly and an energy source; and (e) an energy source for generating an electrical potential difference.

In accordance with the present invention a method for treating an affected area of a living being's eye is disclosed comprising the steps of: (a) associating an aptamer with an ocular iontophoretic device; (b) positioning at least a portion of the ocular iontophoretic device on the eye of the living being; and (c) iontophoretically delivering the aptamer to an affected area of the living being's eye.

The present invention further discloses a method for inhibiting VEGF function within an affected area of a living being's eye comprising the steps of: (a) associating an aptamer with a matrix of an ocular iontophoretic device; (b) associating the ocular iontophoretic device having an active electrode assembly with the eye of the living being; (c) iontophorectically delivering an effective amount of the aptamer to an affected area of the living beings' eye having an amount of VEGF; (d) binding the effective amount of aptamer to the amount of VEGF; and (e) inhibiting function of the amount of VEGF.

BRIEF DESCRIPTION OF THE DRAWINGS

The invention will now be described with reference to the drawings wherein.

DETAILED DESCRIPTION OF THE INVENTION

Figure 1:
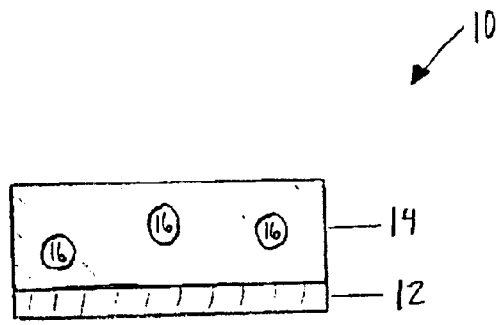
FIG. 1 of the drawings is a cross-sectional schematic representation of a first embodiment of an ocular iontophoretic device fabricated in accordance with the present invention.

While this invention is susceptible of embodiment in many different forms, there is shown in the drawings and will herein be described in detail several specific embodiments with the understanding that the present disclosure is to be considered as an exemplification of the principles of the invention and is not intended to limit the invention to the embodiments illustrated.

Referring now to the drawings and to FIG. 1 in particular, a first embodiment of an ocular iontophoretic device 10 is shown, which generally comprises active electrode assembly 12 and matrix 14. It will be understood that FIG. 1 is merely a cross-sectional schematic representation of ocular iontophoretic device 10. As such, some of the components have been distorted from their actual scale and for pictorial clarity. As will be discussed in greater detail below, ocular iontophoretic device 10 is configured for delivering an aptamer to an affected area of a living being's eye for inhibiting VEGF function in and proximate to the affected area. By inhibiting VEGF function, diseases associated with angiogenesis and/or neovasculation can be remedied— especially including diseases of the eye wherein the affected area is toward the back of the eye, or generally proximate the optic nerve. Ocular iontophoretic device 10 offers many advantages over the previously discussed prior art devices and associated methods, including, but not limited to, simultaneous enablement of non-invasive and deep aptamer delivery, non-invasive local delivery of an effective, therapeutic level of aptamer while minimizing systemic concentrations, and enablement of sclera loading for prolonged delivery into regions in the back of the eye.

Active electrode assembly 12 generally comprises a conductive material, which upon application of an electrical potential difference thereto, drives an ionic aptamer (i.e. an ionic medicament), received from matrix 14 and delivers the aptamer into predetermined tissues and surrounding of a living being. It will be understood that active electrode assembly 12 may comprise an anode or a cathode depending upon whether the medicament is cationic or anionic in form. As would be readily understood to those having ordinary skill in the art, any one of a number of conventional active electrode assemblies are contemplated for use in accordance with the present invention. The only contemplated limitation relative to active electrode assembly 12 is that it must be geometrically and compositionally compatible for ocular applications of living beings, most relevantly humans.

Matrix 14 extends contiguously from active electrode 12, and is preferably fabricated from a material capable of temporarily retaining ionic aptamer 16 in solution. The solution may also contain supplemental agents, such as electrolytes, stability additives, medicament preserving additives, pH regulating buffers, PEGylating agents, etc. Matrix 14 may comprise, for example, a natural or synthetic amorphous member, a natural or synthetic sponge pad, a natural or synthetic lint free pad—just to name a few. Indeed, as would be readily understood to those having ordinary skill in the art, numerous other conventional materials are also suitable for use in accordance with matrix 14 of the present invention. As with active electrode assembly 12, the only contemplated limitation relative to matrix 14 is that it must be geometrically and compositionally compatible for ocular applications of living beings, most relevantly, humans.

Aptamer 16 is retained within matrix 14. In accordance with the present invention, ionic medicament 16 comprises an aptamer which is capable of inhibiting VEGF. Such an aptamer consists of one or more oligonucleotides, which are generally small, specialized polymers of nucleic acids. Preferably, the aptamer is capable of inhibiting one or more isoforms of VEGF, including VEGF-121, VEGF-165, VEGF-189, and VEGF-206. Most preferably, the aptamer is capable of inhibiting VEGF-165. Numerous examples of suitable aptamers for use in accordance with the present invention include those disclosed in U.S. Pat. Nos. 5,859, 228, 5,849,479, and 5,811,533, including the references cited therein. Other aptamers that would be known to those having ordinary skill in the art having the present disclosure before them are likewise contemplated for use. It has been found that in order for the aptamer to be functionally compatible for ocular applications, both its concentration should be adjusted to between approximately 0.1 mg and approximately 10 mg of aptamer per ml of water, and the water should be buffered to a pH ranging between approximately 6.5 and approximately 8.5.

Matrix 14 may optionally include a PEGylating agent, reversibly attached to an aptamer, which slows enzymatic tissue digestion of aptamer 16 upon delivery of the same to an affected area of a living being's eye. Such PEGylating agents include those commercially available from Shearwater Polymers, Inc., of Huntsville, Ala. Of these, those which provide a single functional group for attachment through a linkage at the 5' position and end of the aptamer are preferred. Those with isocyanate or amino functional groups may readily attach to the 5' position. Those with molecular weights in the range of between approximately 5 and approximately 40 kD are preferred. It will be understood that other PEGylating agents known to those having ordinary skill in the art having the present disclosure before them are likewise contemplated for use.

Figure 2:
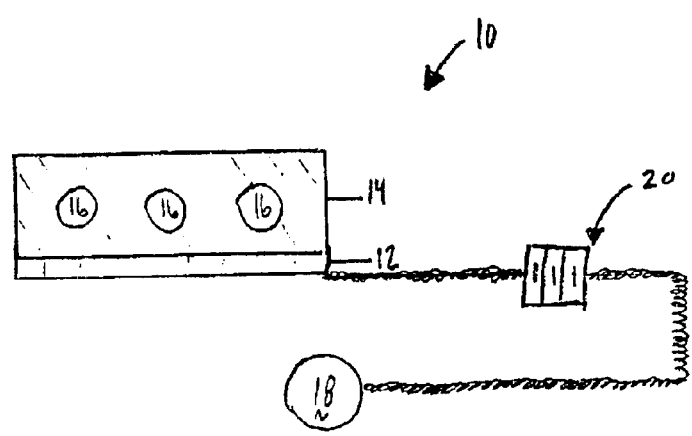
FIG. 2 of the drawings is a cross-sectional schematic representation of a first embodiment of an ocular iontophoretic device fabricated in accordance with the present invention showing the association of a counter electrode assembly and an energy source.

As is shown in FIG. 2, ocular iontophoretic device 10 may also include counter electrode assembly 18 and energy source 20. Counter electrode assembly 18 may be housed within ocular iontophoretic device 10, or alternatively, may be remotely associated with ocular iontophoretic device 10 via conventional electrical conduit. Counter electrode assembly 18 is configured for completing an electrical circuit between active electrode assembly 12 and an energy source 20. As with active electrode 12, counter electrode 18 may comprise an anode or a cathode depending upon whether the medicament is cationic or anionic in form. As would be readily understood to those having ordinary skill in the art, any one of a number of counter electrodes are contemplated for use in accordance with the present invention.

Similarly to counter electrode assembly 18, energy source 20 may be housed within ocular iontophoretic device 10, or alternatively, may be remotely associated with ocular iontophoretic device 10 via conventional electrical conduit. Energy source 20 preferably supplies low voltage constant direct current between approximately 0.1 milliamps (mA) and approximately 4 mA for generating an electrical potential difference. The energy source may also provide for an initial higher voltage during current ramp-up to break down higher initial tissue resistance as in commercial power supply units used for transdermal iontophoresis. For purposes of the present disclosure, energy source 20 may include one or more primary or secondary electrochemical cells. While specific examples of energy source 20 have been disclosed, for illustrative purposes only, it will be understood that other energy sources known to those having ordinary skill in the art having the present disclosure before them are likewise contemplated for use.

Figure 3:
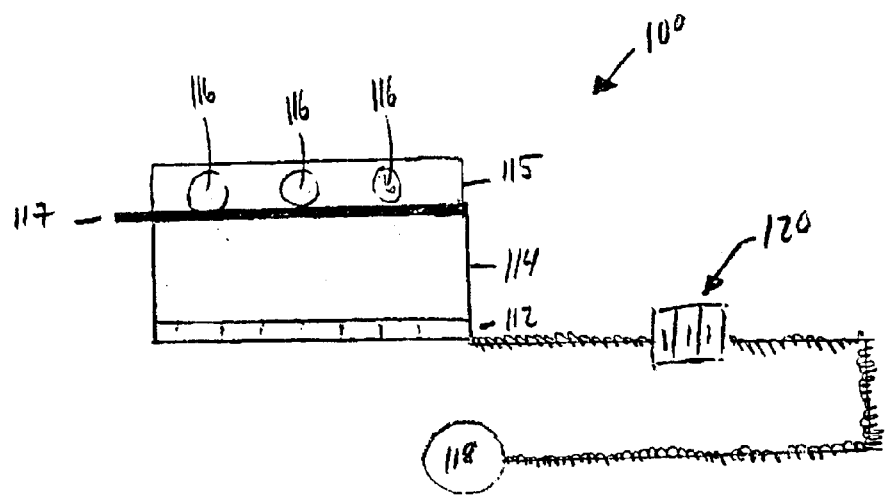
FIG. 3 of the drawings is a cross-sectional schematic representation of a second embodiment of an ocular iontophoretic device fabricated in accordance with the present invention.

Referring now to the drawings and to FIG. 3 in particular, a second embodiment of an ocular iontophoretic device 100 is shown, which generally comprises active electrode assembly 112, matrix 114, reservoir 115, counter electrode assembly 118, and energy source 120. It will be understood that active electrode assembly 112, matrix 114, counter electrode assembly 118, and energy source 120, are configured analogously to previously discussed active electrode assembly 12, matrix 14, counter electrode assembly 18, and energy source 20, respectively. Ocular iontophoretic device 100 is configured for delivering an aptamer to an affected area of a living being's eye for inhibiting VEGF function therein.

Reservoir 115 includes an aptamer 116, in solution, which is capable of inhibiting VEGF function. Reservoir 115 may include a releasable cover member 117 which, upon articulation, releases aptamer 116 into matrix 114. Such a release cover enables prompt delivery of the aptamer with very little device preparation.

The present invention is also directed to a method for treating an affected area of a living being's eye comprising the following steps. First, an aptamer is associated with an ocular iontophoretic device. Preferably the apatmer is metered from a syringe or single unit dose. In this step, the aptamer is preferably capable of inhibiting VEGF function, including the isoforms VEGF-121, VEGF-165, VEGF-189, and VEGF-206. Second, at least a portion of the ocular iontophoretic device is positioned on the eye of a living being. Finally, the aptamer is iontophoretically delivered to an affected area of the living being's eye. Preferably, the delivery lasts for between approximately 1 and approximately 60 minutes. Compared to prior art administration or delivery methods, the present invention enables a generally painless, non-invasive and deep delivery of the aptamer. Moreover, the aptamer is locally delivered to an affected area of a living being's eye at an effective, therapeutic level. Preferred ocular delivery regions include the vitreous humor, retina, choroid, circulation of the retina, circulation of the choroid, and sclera. It is likewise contemplated that delivery to front regions of the eye may be administered.

As previously discussed, certain ocular diseases may require the association of a PEGylating agent with the aptamer to slow enzymatic tissue digestion of the aptamer upon delivery of the same to an affected area of a living being's eye. In addition, the aptamer is preferably present in a concentration between approximately 0.1 mg and approximately 10 mg of aptamer per ml of water, wherein the water is buffered to a pH ranging between approximately 6.5 and approximately 8.5.

The present invention is also directed to a method for inhibiting VEGF function within an affected area of a living being's eye comprising the following steps. First, an aptamer is associated with the matrix of the ocular iontophoretic device. Second, an effective amount of the aptamer is iontophoretically delivered to an affected area of the living being's eye having an amount of VEGF. Third, the effective amount of aptamer is bound or attached to the amount of VEGF. Fourth, the function of the amount of VEGF is inhibited.

The foregoing description merely explains and illustrates the invention and the invention is not limited thereto except insofar as the appended claims are so limited, as those skilled in the art who have the disclosure before them will be able to make modifications without departing the scope of the invention.

What is claimed is:

1. A method for treating an affected area of a living being's eye, comprising the steps of:
    associating an aptamer present in a concentration between approximately 0.1 mg and approximately 10 mg of aptamer per ml of water with an ocular iontophoretic device, wherein the water is buffered to a pH ranging between approximately 6.5 and approximately 8.5;
    positioning at least a portion of the ocular iontophoretic device on the eye of a living being; and
    iontophoretically delivering the aptamer to an affected area of the living being's eye.

2. The method according to claim 1, wherein the step of associating the aptamer includes the step of associating an aptamer capable of inhibiting VEGF function.

3. The method according to claim 1, wherein the step of associating the aptamer includes the step of associating an aptamer capable of inhibiting at least one VEGF selected from the group consisting of VEGF-121, VEGF-165, VEGF-189, and VEGF-206.

4. The method according to claim 1, wherein the step of associating the aptamer includes the step of associating an aptamer capable of inhibiting VEGF-165.

5. The method according to claim 1, wherein the step of iontophoretically delivering the aptamer, includes the step of iontophoretically delivering the aptamer to at least one of the group consisting of the vitreous humor, retina, choroid, circulation of the retina, circulation of the choroid, and sclera.

6. The method according to claim 1, wherein the step of iontophoretically delivering the aptamer, includes the step of iontophoretically loading a sclera of the living being's eye with the aptamer for prolonged delivery into back regions of the living being's eye.

7. The method according to claim 1, wherein the step of iontophoretically delivering the aptamer, includes the step of iontophoretically delivering the aptamer at a current between approximately 0.1 mA and approximately 4 mA for a period of between approximately 1 and approximately 60 minutes.

8. The method according to claim 1, wherein the step of iontophoretically delivering the aptamer, includes the step of delivering the aptamer using negative polarity electrical current.

9. The method according to claim 1, wherein the step of positioning at least a portion of the ocular iontophoretic device on the eye of a living being includes the step of applying at least a portion of the ocular iontophoretic device to a conjunctival surface in a region of a pars planum.

10. A method for treating an affected area of a living being's eye, comprising the steps of:

associating an aptamer with an ocular iontophoretic device;

associating a PEGylating agent with the aptamer positioning at least a portion of the ocular iontophoretic device on the eye of a living being; and iontophoretically delivering the aptamer to an affected area of the living being's eye.

11. The method according to claim 10, wherein the step of associating a PEGylating agent includes the step of associating a PEGylating agent comprising a moiety selected from the group consisting of isocyanates, amino groups, and mixtures thereof.

12. A method for inhibiting VEGF function within an affected area of a living being's eye, comprising the steps of:

associating an aptamer present in a concentration between approximately 0.1 mg and approximately 10 mg of aptamer per ml of water with a matrix of an ocular iontophoretic device, wherein the water is buffered to a pH ranging between approximately 6.5 and approximately 8.5;

associating the ocular iontophoretic device having an active electrode assembly with the eye of the living being;

iontophorectically delivering an effective amount of the aptamer to an affected area of the living being's eye having an amount of VEGF;

binding the effective amount of aptamer to the amount of VEGF; and inhibiting function of the amount of VEGF.

13. The method according to claim 12, wherein the step of associating the aptamer includes the step of associating an aptamer capable of inhibiting VEGF function.

14. The method according to claim 12, wherein the step of associating the aptamer includes the step of associating an aptamer capable of inhibiting at least one VEGF selected from the group consisting of VEGF-121, VEGF-165, VEGF-189, and VEGF-206.

15. The method according to claim 12, wherein the step of associating the aptamer includes the step of associating an aptamer capable of inhibiting VEGF-165.

16. The method according to claim 12, wherein the step of iontophoretically delivering the aptamer, includes the step of iontophoretically delivering the aptamer to at least one of the group consisting of the vitreous humor, retina, choroid, circulation of the retina, circulation of the choroid, and sclera.

17. The method according to claim 12, wherein the step of iontophoretically delivering the aptamer, includes the step of iontophoretically loading a sclera of the living being's eye with an effective amount of the aptamer for prolonged delivery into back regions of the living being's eye.

18. The method according to claim 12, wherein the step of iontophoretically delivering the aptamer, includes the step of iontophoretically delivering an effective amount of the aptamer at a current between approximately 0.1 mA and approximately 4 mA for a period of between approximately 1 and approximately 60 minutes.

19. The method according to claim 12, wherein the step of iontophoretically delivering the aptamer, includes the step of delivering the aptamer using negative polarity electrical current.

20. The method according to claim 12, wherein the step of associating the ocular iontophoretic device having an active electrode assembly with the eye of the living being includes the step of applying at least a portion of the ocular iontophoretic device to a conjunctival surface in a region of a pars planum.

21. A method for inhibiting VEGF function within an affected area of a living being's eye, comprising the steps of:

associating an aptamer with a matrix of an ocular iontophoretic device;

associating a PEGylating agent with the aptamer;

associating the ocular iontophoretic device having an active electrode assembly with the eye of the living being;

iontophorectically delivering an effective amount of the aptamer to an affected area of the living being's eye having an amount of VEGF;

binding the effective amount of aptamer to the amount of VEGF; and inhibiting function of the amount of VEGF.

22. The method according to claim 21, wherein the step of associating a PEGylating agent includes the step of associating a PEGylating agent comprising a moiety selected from the group consisting of isocyanates, amino groups, and mixtures thereof.

* * * * *